United States Patent [19]

Lapka et al.

[11] Patent Number: 4,622,244
[45] Date of Patent: Nov. 11, 1986

[54] PROCESS FOR PREPARATION OF MICROCAPSULES

[75] Inventors: Galen G. Lapka, Belleville, Ill.; Norbert S. Mason, Clayton; Curt Thies, Ballwin, both of Mo.

[73] Assignee: The Washington University, St. Louis, Mo.

[21] Appl. No.: 643,547

[22] Filed: Aug. 23, 1984

Related U.S. Application Data

[60] Division of Ser. No. 72,079, Sep. 4, 1979, abandoned, which is a continuation-in-part of Ser. No. 9,875, Feb. 7, 1979, abandoned, which is a continuation of Ser. No. 846,689, Oct. 31, 1977, abandoned, which is a continuation of Ser. No. 648,907, Jan. 14, 1976, abandoned, which is a division of Ser. No. 566,270, Apr. 9, 1975, abandoned, which is a continuation-in-part of Ser. No. 449,042, Mar. 7, 1974, abandoned.

[51] Int. Cl.⁴ ............................................... B01J 13/02
[52] U.S. Cl. .................................. 427/213.32; 424/19; 424/33; 424/35; 427/213.36; 428/402.24; 514/811; 514/812; 514/963
[58] Field of Search ...................... 427/213.32, 213.36; 428/402.24; 424/19, 33, 35

[56] References Cited

U.S. PATENT DOCUMENTS

| | | | |
|---|---|---|---|
| 3,173,878 | 3/1965 | Reyes | 252/182 X |
| 3,336,155 | 8/1967 | Rowe | 428/402.24 X |
| 3,415,758 | 12/1968 | Powell et al. | 428/402.24 X |
| 3,773,919 | 11/1973 | Boswell et al. | 424/19 |
| 3,887,699 | 6/1975 | Yolles | 424/32 X |
| 3,914,402 | 10/1975 | Shell | 424/37 X |
| 4,166,800 | 9/1979 | Fong | 424/19 X |

*Primary Examiner*—Richard D. Lovering
*Attorney, Agent, or Firm*—Senniger, Powers, Leavitt and Roedel

[57] ABSTRACT

Microcapsules particularly those less than 300 microns in size are provided which are adapted for injection by conventional means to afford controlled release of the encapsulated drug material, such as a narcotic antagonist, an antibiotic or the like, over a prolonged period. The microcapsules are characterized by a solid core material of a solid, injectable drug material and a wall material engulfing the core material and composed of a polymer material such as a bioabsorbable polymer material. The microcapsules are made by providing a system containing a mixture of particles of a solid, injectable drug material and a solution of a bioabsorbable polymer material in a solvent in which the drug material is substantially insoluble. The system is treated to induce phase separation of the bioabsorbable polymer material from the solution by the addition to the system of a phase separation agent at a temperature at least as low as $-30°$ C. Phase separation may also be carried out at room temperature, but in either event, isolation of the microcapsules formed during the phase separation should be carried out at a temperature at least as low as $-30°$ C. The system is maintained in an agitated condition until the walls of the microcapsules constituted by the bioabsorbable polymer are substantially solidified in order to avoid aggregation or agglomeration of the microcapsules into larger capsules. The microcapsules are ready for injection, for example by being suspended in an aqueous suspending medium, upon being isolated from the system.

16 Claims, No Drawings

PROCESS FOR PREPARATION OF MICROCAPSULES

CROSS-REFERENCE TO RELATED APPLICATION

This application is a divisional application of application Ser. No. 072,079 filed Sept. 4, 1979, now abandoned, which is a continuation-in-part of our copending, coassigned U.S. patent application Ser. No. 9,875 filed Feb. 7, 1979, now abandoned which is a continuation of application Ser. No. 846,689, filed Oct. 31, 1977, now abandoned which is a continuation of application Ser. No. 648,907, filed Jan. 14, 1976, now abandoned, which is a division of application Ser. No. 566,270, filed Apr. 9, 1975, now abandoned, which is a continuation-in-part of our coassigned U.S. patent application Ser. No. 449,042, filed Mar. 7, 1974, now abandoned.

BACKGROUND OF THE INVENTION

The present invention relates to the field of microencapsulation and, more particularly, to methods of making injectable microcapsules of a solid, injectable drug material and the microcapsules made thereby.

The art of microencapsulation has developed various processes for individually coating particulate matter for protection against deleterious influences. The encapsulated material may be subsequently released under controlled conditions. A number of chemical microencapsulation processes are based upon the principles of coacervation which is the term used to denote the phenomenon of phase separation in polymer solutions resulting in the formation of two or more more liquid phases. Such processes are described, for example, in U.S. Pat. Nos. 2,800,457, 2,800,458, 3,041,289, 3,341,466, 3,415,758, 3,429,827, 3,594,327, 3,639,256 and 3,674,704. An encapsulation process using coacervation may be generally regarded as involving three steps. First, a three-phase system is established with a liquid vehicle constituting the continuous phase and the coating material and material to be coated constituting disperse phases. Next, liquid polymeric material is deposited around the material to be coated. Finally, the polymeric coating material is hardened or solified.

Encapsulation processes have been employed for encapsulating a large variety of materials such as food products, chemicals of various types, fuels, adhesives, paints and detergents. In the pharmaceutical field, encapsulation techniques have been used to mask the unpleasant taste of certain drugs, to impart improved stability to drugs which are subject to deterioration in the presence of atmospheric moisture and oxygen, and to delay the release of drugs orally ingested into the body. Thus, U.S. Pat. No. 3,155,590 discloses a process for encapsulation of acetylsalicylic acid (aspirin) particles to produce capsules which provide sustained release of the aspirin in the human alimentary canal. Such oral preparations possess limited time release capabilities.

In recent years, there has been an interest in developing long-acting delivery systems for injectable drug materials. For example, efforts have been made to develop means of delivering injectable narcotic antagonists such as cyclazocine (3-(cyclopropylmethyl)-1,2,3,4,-5,6-hexahydro-6,11-dimethyl-2,6-methano-3-benzazocin-8-ol) to drug addict patients over a prolonged period at a relatively constant rate. These efforts have led to the development of composites of cyclazocine with certain polymeric materials in the form of films or particles made by grinding the films for surgical implantation or hypodermic injection (see Yolles et al. "Long-Acting Delivery Systems for Narcotic Antagonists", J. Med. Chem. 16, 897 (1973)), but the composite particles used were too large for injection by means of the relatively small needles (e.g., 22 to 18 gauge) commonly employed by the medical profession and did not provide complete encapsulation for the narcotic antagonist.

Scribner U.S. Pat. No. 3,755,558 (Aug. 28, 1973) and Boswell et al. U.S. Pat. No. 3,773,919 (Nov. 20, 1973) each contain identical disclosures of a method of purportedly microencapsulating drug particles. Specifically, these patents disclose suspension of 0.5 to 25 micron drug particles in chloroform (in which they are not soluble) containing a polylactide polymer mixture in solution at such a concentration as to give a low-viscosity solution. A miscible solvent in which the polymer is not soluble, such as hexane, is then added slowly to precipitate the polymer. The coated particles are filtered and washed with hexane and allowed to dry. In our hands, however, it has been found that this procedure does not produce true microcapsules less than 300 microns in size but rather drug-polymer aggregates.

There has remained, therefore, an unfulfilled need for a practical and effective method for making microcapsules of a solid, injectable drug material with the microcapsules being less than 300 microns in size and being adapted for injection by conventional means so as to provide for delayed and sustained release of the drug material over a prolonged period.

SUMMARY OF THE INVENTION

Among the several objects of the invention, therefore, may be noted the provision of microcapsules such as microcapsules of a solid, injectable drug material encapsulated by a wall material constituted by a bioabsorbable polymer material; the provision of microcapsules which are of such minute size as to be adapted for injection by conventional means and which provide for sustained time release of the encapsulated drug material; the provision of microcapsules of the character described which are suitable for injection intramuscularly or subcutaneously with minimal tissue irritation effects; the provision of novel and practical processes for making microcapsules; and the provision of such processes which may be conveniently and economically carried out for the production of the desired microcapsules. Other objects and features will be in part apparent and in part pointed out hereinafter.

In one aspect, the present invention is directed to a process for the preparation of microcapsules having a particulate core material encapsulated by a polymeric coating wherein the polymer is dissolved in a solvent in which the core material is not soluble and the polymer is precipitated by phase separation to encapsulate the core material by the addition of a phase separation agent to the polymer-core material-solvent system, the improvement comprising the addition of the phase separation agent to the polymer-core material-solvent system to cause phase separation of the polymer at a temperature at least as low as −30° C. In another aspect, the present invention is directed to a process wherein the microcapsules formed during phase separation, whether phase separation is effected at room temperature or at reduced temperatures, are isolated at a temperature at least as low as −30° C. In still another aspect, the invention is directed to a process wherein both phase separation and isolation of the microcapsules are effected at a temperature at least as low as $-30°$ C. The invention is also directed to the novel microcapsules made by the processes of the invention.

DESCRIPTION OF THE PREFERRED EMBODIMENTS

In accordance with the present invention, a practical means has now been found for producing microcapsules such as microcapsules of a solid, injectable drug core material of a size which renders them suitable for injection by means of the relatively small needles (e.g., 22 to 18 gauge) customarily employed in medical practice thereby achieving controlled or sustained release of the drug material. In the practice of our invention, particles of a solid, injectable drug material are first mixed with a solution of a polymer such as a bioabsorbable polymer material dissolved in a solvent in which the drug material is substantially insoluble. The resulting mixture is then treated by the addition of a phase separation agent to induce phase separation of the polymer material from the solution and thereby form a liquid coacervate. By liquid coacervate is meant the phase which has the highest proportion of the polymer. Thus, a system is produced in which the continuous phase is depleted of the polymer and the liquid coacervate containing most of the said polymer constitutes the discontinuous phase. The liquid coacervate so formed wets and coats the core material (e.g., solid injectable drug material) to produce microcapsules less than 300 microns in size in which the drug material constitutes the core material and the polymer material (e.g., bioabsorbable polymer) constitutes the wall material. Upon being isolated, the microcapsules are ready for injection without further processing. For injection purposes, the microcapsules are preferably suspended in an aqueous or oil suspending medium for injection. Throughout the manufacturing steps described above, the system is maintained in an agitated condition, as by mechanical stirring, until the walls of the microcapsules constituted by the bioabsorbable polymer material are substantially solidified or hardened.

In one aspect of the invention, we have found that it is important for the production of true and useful microcapsules that the microcapsules formed by the phase separation step, whether phase separation is carried out at room temperature (25° C.) or at reduced temperatures (e.g., $-30°$ C. to $-70°$ C.), be isolated at a temperature at least as low as $-30°$ C. Preferably, isolation is carried out at a temperature of from about $-30°$ C. to about $-70°$ C. with the latter temperature being particularly preferred and being achieved through the use of a dry ice/isopropanol mixture. Through the use of such reduced temperatures, agglomeration or stickiness of the microcapsules is substantially avoided.

In a second aspect of the invention, we have found that while the phase separation step may be carried out at room temperature or at reduced temperatures provided the microcapsules formed during phase separation are isolated at the reduced temperatures set forth above, it is advantageous from the standpoint of microcapsule yield and avoidance of agglomeration to carry out the phase separation step by the addition of a phase separation agent at a temperature at least as low as $-30°$ C. Again, the temperature for effecting phase separation is preferably from about $-30°$ C. to about $-70°$ C. with the latter temperature being especially preferred.

As indicated, phase separation can be carried out at room temperature or at temperatures down to approximately $+4°$ C. so long as the isolation of the microcapsules formed during phase separation is effected at the reduced temperatures set forth above. However, as shown by the experimental data set forth hereinafter, poor capsules are obtained when both the phase separation and isolation steps are carried out at room temperature.

In another aspect of the invention, it is preferred that both the phase separation and isolation steps are carried out at a temperature at least as low as $-30°$ C. and more generally at a temperature of about $-30°$ C. to about $-70°$ C. Even lower temperatures may be utilized in both the phase separation and isolation steps but are not normally deemed necessary.

Although the invention is more fully described hereinafter with particular reference to the microencapsulation of drug materials, it will be understood that the invention is also applicable to the microencapsulation of other materials.

Since the microcapsules of the invention wherein the core material is a drug are prepared for injection to provide controlled release of the encapsulated drug material, it is essential in that embodiment of the invention that the walls of the capsules be constituted by one or more bioabsorbable polymer materials which are physiologically compatible with the body. Bioabsorbability is understood to be that property of a polymer which enables the body or a living system to transform it slowly but completely into nontoxic products with little or no immunologic response. A number of such polymer materials are known to the art and have been utilized, for example, as materials of construction for surgical implants. Among the bioabsorbable polymer materials suitable for use in the invention may be mentioned poly(lactic acid) or polylactic acid polymers, such as dl-poly(lactic acid) (or poly(dl-lactic acid)) and L+-poly(lactic acid) or poly(L+)-lactic acid)) polymers, poly-(glycolic acid) polymers, poly(hydroxybutyric acid) polymers and lactide/glycolide copolymers. Such bioabsorbable polymer materials and their preparation have been described in the literature (Kulkarni et al. "Polylactic Acid for Surgical Implants", Arch. Surg. Vol. 93, p. 839, Nov. 1966; Kulkarni et al. "Biodegradable Poly(lactic acid) Polymers", J. Biomed. Mater. Res. Vol. 5, p. 169 (1971); Chujo et al. "Ring-Opening Polymerization of Glycolide", Die Makromolekulare Chemie 100 (1967) 262-266; and Chujo et al. "Physical and Chemical Characteristics of Polyglycolide", Die Makromolekulare Chemie 100 (1967) 267-270). The particular bioabsorbable polymer materials listed above are to be regarded as merely illustrative of the class of such materials and it will be understood that other bioabsorbable polymer materials may also be satisfactorily used in the practice of the invention.

The solid injectable drug material which constitutes the core material of the microcapsules may be any such injectable drug material for which it is desired to establish a long-acting, sustained release delivery system. Thus, the solid, injectable drug material may be a narcotic antagonist, such as cyclazocine, an antibiotic, such as tetracycline, a birth control agent, such as ethisterone, a cardiovascular agent, such as digitoxin, an alcohol-sensitizing agent, such as citrated calcium cyanamide, or a drug such as antimony potassium tartrate, used for the treatment and prophylaxis of schistosomiasis and trypanosomiasis or other drugs such as salmon calcitonin, ACTH, lypressin, sommatostatin and insulin. In short, the invention is generally applicable to the encapsulation of solid, injectable drug materials for human or veterinary use.

In carrying out the invention, the solubility behavior of the particular injectable drug material to be encapsulated and the particular bioabsorbable polymer material to be used as the capsule wall material must be determined. On the basis of solubility data obtained by routine experimentation, a solvent is selected in which the bioabsorbable polymer material is substantially soluble but in which the drug material is substantially insoluble. The solvent meeting these criteria functions as the continuous phase in the encapsulation method of the invention.

For example, taking cyclazocine as the solid, injectable drug material, Table I summarizes the solubility data obtained for this drug in a number of solvents.

TABLE I

| | Solubility Behavior of Cyclazocine | | |
|---|---|---|---|
| | | Solubility, g/100 ml. | |
| Solvent | 4° C. | 25° C. | (Elevated Temp.), °C. |
| decahydronaphthalene | — | 0.17 | 0.34 (130° C.) |
| cyclohexane | — | — | Insoluble (80° C.) |
| chloroform | — | 0.76 | — |
| xylene | — | 0.12 | 0.18 (50° C.); 1.75 (90° C.) |
| toluene | — | 0.10 | 0.15 (35° C.); 0.40 (50° C.) |

TABLE I-continued

| | Solubility Behavior of Cyclazocine | | |
|---|---|---|---|
| | | Solubility, g/100 ml. | |
| Solvent | 4° C. | 25° C. | (Elevated Temp.), °C. |
| methanol | — | 1.84 | 3.32 (63° C.) |
| acetone | — | 0.51 | — |
| ethanol | — | 0.664 | 5.2 (73° C.) |
| 75 acetone/25 ethanol (V/V) | — | 0.474 | — |
| 50 acetone/50 ethanol (V/V) | — | 0.470 | — |
| 25 acetone/75 ethanol (V/V) | — | 0.454 | — |

These data were obtained by adding 0.1 g cyclazocine to 5 ml. of solvent and adjusting the system to the desired temperature. After equilibration (20–30 min), one ml. of solution was transferred to a tared weighing dish and the solids content determined by solvent evaporation.

As the results show, cyclazocine has relatively low solubility in a range of solvents at room temperature. In particular, the aromatic solvents have little tendency to dissolve it at room temperature. The results also show that solubility increases significantly in most cases at elevated temperatures.

Tables II and III contain the solubility data obtained for various bioabsorbable polymer materials.

TABLE II

| | Solubility of Bioabsorbable Polymers in Relatively Polar Solvents | | | | | | | | |
|---|---|---|---|---|---|---|---|---|---|
| | | | | Solubility, g./100 ml. | | | | | |
| | Inherent | Acetone | Ethanol | | Ethyl Acetate | | | Methyl Ethyl Ketone | |
| Polymer | Viscosity* | (25° C.) | 25° C. | 75° C. | 0° C. | 25° C. | 75° C. | 25° C. | 75° C. |
| dl-poly(lactic acid) | .158 | >2.0 | — | — | — | — | — | — | — |
| dl-poly(lactic acid) | .819 | >2.0 | 0.01 | 0.17 | — | — | — | — | — |
| L+-poly(lactic acid) | — | — | — | — | — | 2.3 | 11.2 | 0.25 | 17.2 |
| 75/25(w/w) lactide/ glycolide copolymer | — | — | — | — | >2.0 | >2.0 | — | — | — |
| 50/50(w/w) lactide/ glycolide copolymer | — | — | — | — | — | 0.92 | 1.09 | 0.07 | 0.34 |
| 25/75(w/w) lactide/ glycolide copolymer | | | | | | | | | |

*Measured in benzene at 30° C. (1 wt. % soluion)

TABLE III

| | Solubility of Bioabsorbable Polymers in Relatively Nonpolar Solvents | | | | | | | | |
|---|---|---|---|---|---|---|---|---|---|
| | | | | | Solubility, g./100 ml. | | | | |
| | Inherent | Decahydro- naphthalene | Mineral Spirits | | Benzene | Toluene | | Xylene | |
| Polymer | Viscosity* | (130° C.) | 25° C. | 150° C. | (25° C.) | 25° C. | 100° C. | 25° C. | 100° C. |
| dl-poly(lactic acid) | .158 | — | 0.26 | 0.22 | — | >2.0 | — | — | — |
| dl-poly(lactic acid) | .819 | Insol. | — | — | >2.0 | >2.0 | — | >2.0 | — |
| L+-poly(lactic acid) | — | Insol. | — | — | — | 1.5 | 17.0 | — | >2.0 |
| | | Insol. | — | — | >2.0 | (>2.0 at 70° C.) | — | — | Insol. |
| 75/25(w/w) lactide/ glycolide copolymer | — | Insol. | — | — | — | — | — | — | Insol. |
| 50/50(w/w) lactide/ glycolide copolymer 25/75(w/w) lactide/ glycolide copolymer | — | — | — | — | — | 0.1 | 1.08 | — | — |

*Measured in benzene at 30° C. (1 wt. % solution)

Solubilities of the polymer materials were determined by adding 0.1 g. polymer to 5 ml. of solvent and agitating the mixture at constant temperature until the sample dissolved or until no further change occurred. If the polymer dissolved, then the entry in the above tables is:

| | | | 1.5 (100° C.) |
|---|---|---|---|
| benzene | — | 0.14 | 0.24 (50° C.) |
| methyl ethyl ketone | 0.91 | 1.6 | 5.98 (79° C.) |
| ethyl acetate | 0.26 | 0.63 | 4.50 (77° C.) |
| n-butanol | 0.45 | 1.5 | 21.5 (117° C.) |
| isopropanol | — | 2.68 | 2.68 (80° C.) |

"2 g./100 ml.". If it did not all dissolve, a 1 ml. aliquot of the solution was taken and the solids content determined after solvent evaporation. In the above tables, whenever a specific polymer solubility is given, an excess of polymer was added to 5 ml. of solvent. A 1 ml. aliquot of the solution was then taken and the solids content determined after solvent evaporation.

From the above solubility data, it can be seen that a number of bioabsorbable polymers are soluble in various solvents in which cyclazocine solubility is low. Thus, these data show that where dl-poly(lactic acid) polymer material is to be used for encapsulating cyclazocine, benzene, toluene, xylene and acetone may be used as solvents for the polymer. All of these solvents dissolve dl-poly(lactic acid) polymer at 25° C. in concentrations 2.0 wt. %, an amount of polymer sufficient for coacervation to occur.

Similar solubility data may be readily developed for any particular injectable drug-bioabsorbable polymer combination.

Once the solubility characteristics for a specific drug material-bioabsorbable polymer combination have been established, a system of the two materials is prepared by dissolving the bioabsorbable polymer in a solvent in which the solid, injectable drug material is substantially insoluble and adding particles of the drug material thereto with stirring to maintain the mixture in an agitated condition. The resulting system is then treated by the addition of a phase separation agent to induce phase separation of the bioabsorbable polymer material from the solution thereby forming a liquid coacervate which wets and coats or engulfs the particles of the particles of the solid drug material. In accordance with the invention, we have found that phase separation must be induced so as to form a coacervate phase which is initially liquid and which wets and coats the drug to be encapsulated. The coacervate phase when initially formed must not be gelatinous in nature or constituted by a solid precipitate of the bioabsorbable polymer material. For the purposes of the invention, the coacervate phase is thus flowable and constitutes the discontinuous phase with the solution remaining as the continuous phase of the system.

In accordance with the invention, phase separation necessary for the practical production of true microcapsules within the meaning of the present invention can be induced through the addition of a phase separation agent such as an incompatible polymer or oligomer material with or without an accompanying temperature change as previously indicated. A blend of an incompatible polymer with a natural oil (e.g., a glyceride) can also be used. Less desirably, a nonsolvent for the bioabsorbable polymer may serve as the phase separation agent where both the phase separation and isolation steps are carried out at the reduced temperatures previously discussed. In order for the phase separation agent to induce phase separation which in turn will effectively produce useful microcapsules, said phase separation agent should satisfy certain conditions. Thus, it should desirably cause phase separation and the formation of a second phase to occur when its volume percent of the total volume of the system is less than approximately 10%. More preferably, this minimum phase inducer concentration should range between approximately 0.6 and 6.5 volume percent based upon the total volume of the system. Further, the phase separation agent should form a liquid coacervate which has an initial viscosity of less than approximately 1,000 centistokes (measure as hereinafter described in a Cannon-Ubbelohde capillary viscometer), and preferably an initial viscosity between approximately 10 and 300 centistokes. This liquid coacervate should contain a preponderance of the bioabsorbable polymer designed to serve as the capsule wall material. Finally, the phase separation agent should produce a liquid coacervate which both wets and coats (or engulfs) the particles of the solid, drug material to be injected.

Referring to Table IV, there is set forth the results of a number of experimental phase separation runs carried out with various phase separation agents. The bioabsorbable polymer used in each instance was dl-poly(lactic acid) (dl-PLA) having an inherent viscosity of 0.715 (1% by wt. solution in benzene at 30° C.) and an initial concentration in toluene at 3 g./100 ml. In the case of the incompatible polymer materials, the procedure employed was that generally set forth in the working examples appearing hereinafter. One experiment reported in Table IV was carried out by adding hexane to a chloroform solution of dl-PLA following the procedure set forth in column 10, lines 48–56 of U.S. Pat. No. 3,773,919.

Note that in the case of the nonsolvent hexane, a very high volume percent of nonsolvent, based upon the total volume of the system, was required to bring about the initial appearance of the second phase and, correspondingly, the initial viscosity of the PLA-rich or second phase is quite high and continues to increase. This latter condition in particular is not suitable for the production of true microcapsules with a size of less than 300 microns.

In Table IV are also set forth data respecting the properties of the PLA-rich phase formed by a number of phase inducers. In order to prepare useful microcapsules in accordance with the present invention, it is necessary that the phase inducer produce a liquid coacervate which both wets and coats (or engulfs) the individual drug particles. Whether a drug or other substance is wetted by the PLA-rich phase depends upon the relationship of interfacial tensions of the drug with the PLA-rich phase, the drug and supernatant, and the PLA-rich phase with the supernatant, but not upon the initial viscosity of the PLA-rich phase. However, the process of engulfing or wrapping of a drug particle is dependent upon coacervate viscosity. If too viscous, the coacervate phase cannot completely enclose or engulf a drug particle. A specific example is wetting of cyclazocine particles by the highly viscous PLA-rich phase obtained with hexane. Although this phase wets cyclazocine, it was far too viscous (13,400 cs.) for coating or engulfing of individual drug particles. Coating of individual drug particles requires the PLA-rich phase to readily break up into droplets and, for this purpose, the initial viscosity of the PLA-rich or liquid coacervate should be less than approximately 1,000 centistokes. If the initial viscosity of the PLA-rich phase exceeds this level, the phase tends to remain as large globs under the degree of mixing or agitation desirable for microencapsulation. If agitation is increased in an effort to reduce the size of the viscous globs, the higher shear tends to remove the PLA-rich phase from the drug particles and lead to the formation of nonuniform capsules, i.e., capsules with a spotty or fragmentary coating of the bioabsorbable polymer material.

TABLE IV

The properties of dl-PLA-rich phase formed by different phase inducers.*

| Phase Inducer Phase Inducer | PLA Conc. Conc. (vol. %) | PLA Conc. gm./100 ml. | of Total in supernatant | PLA-rich phase Vol. % Conc. Volume | PLA*** viscosity gm./100 ml. | Measured in centistokes |
|---|---|---|---|---|---|---|
| paraffin oil | 8.89 | 2.60 | not detectable | 11.6 | 19.9 | 680 |
| hexane** | 120 | 1.33 | detectable | 4.1 | 32.4 | 13,400 |
| polybutadiene (Lithene PH) | 3.18 | 2.73 | not detectable | 22.5 | 12.2 | — |
| polybutadiene (Butarez NF) | 0.47 | 2.85 | not detectable | 29.3 | 9.7 | — |
| polyisobutylene (Butyl LM430) | 0.98 | 2.86 | not detectable | 47.1 | 6.1 | — |

*Inherent viscosity of the dl-PLA is .715 as measured at 30° C. in benzene (1 wt. % solution).
**PLA dissolved in chloroform instead of toluene
***Calculated on the basis of perfect incompatibility As mentioned, the most desirable range for the initial viscosity of the PLA-rich phase or liquid coacervate is on the order of approximately 10 to 300 centistokes and the preferred concentration for the phase inducer (e.g., an incompatible polymer material) is between approximately 0.6 to 6.5 volume percent based upon the total volume of the system. Also, as indicated, it is essential that the liquid coacervate produced be capable of both wetting and coating (or engulfing) the particular drug particles in order that useful microcapsules be obtained.

Coacervate viscosities given were measured in a Cannon-Ubbelohde capillary viscometer immersed in a water bath controlled at 30±0.1° C. Ten ml. of solution was used. The value of 13,400 cs. in the case of hexane was obtained by timing the movement of a glob of the PLA-rich phase in a verticle ⅛ in. I.D. plastic tube and comparing it to the time of flow of a similar quantity of silicone fluid whose viscosity was 350 cs. The PLA-rich phase flowed 23 mm. in 16 minutes whereas the silicone fluid required 25 seconds to flow the same distance. There was no Oswald pipette or Ubbelohde viscometer available in our laboratory in this high range of viscosity, and therefore both values given in the case of hexane should be considered as approximate orders of magnitude.

Any of a variety of incompatible polymers which meet the above-noted conditions may be employed as phase separation agents in the practice of the invention for the purpose of inducing phase separation of the bioabsorbable polymer from solution. It will be understood that the term "incompatible polymers" includes oligomers of relatively low molecular weight. Among the incompatible polymers useful as phase separation agents may be mentioned liquid polybutadiene polymers or resins such as those marketed under the trade designation "Lithene" by Lithium Corp. of America, including "Lithene AL" (approx. mol. wt. 700–1,000), "Lithene AM" (approx. mol. wt. 1,000–1,500), "Lithene AH" (approx. mol. wt. 1,500–2,000), "Lithene QL" (approx. mol. wt. 500–1,000), "Lithene QM" (approx. mol. wt 1,000–2,000), "Lithene QH" (approx. mol. wt. 2,000–3,000) and "Lithene PH"; liquid butadiene-alphamethylstyrene random copolymers marketed under the trade designation "Lithene YL" (approx. mol. wt. 500-1500) and "Lithene YH" (approx. mol. wt. 1500-3000) by Lithium Corp. of America; liquid polybutadiene homopolymers such as that marketed under the trade designation "Ricon 150" by The Richardson Company of Melrose Park, Ill.; liquid butadiene-styrene copolymers such as the liquid 80/20 butadiene-styrene copolymer marketed under the trade designation "Ricon 100" by The Richardson Company; polyisobutylene polymers such as that marketed under the trade designation "Butyl LM 430" by Exxon Corp. of Linden, N.J.; liquid carboxyl-terminated polybutadiene polymers such as that marketed under the trade designation "Hycar CTB" by B. F. Goodrich Chemical Company of Cleveland, Ohio; liquid butadiene-acrylonitrile polymers such as that marketed under the trade designation "Hycar CTBN" by B. F. Goodrich; high cis 1,4 high molecular weight solid polybutadiene such as that marketed under the trade designation "Ameripol CB 220" by B. F. Goodrich; liquid polybutadiene polymers such as those marketed under the trade designations "Butarez CTL", "Butarez HTS" and "Butarez NF" by Phillips Petroleum Company of Bartlesville, Okla.; liquid polybutadiene homopolymers such as those marketed under the trade designation "Poly bd R-45M" and "Poly bd R-45HT" by Arco Chemical Company of Philadelphia, Pa.; styrene-butadiene copolymers such as that marketed under the trade designation "Poly bd CS-15" by Arco Chemical; acrylonitrile-butadiene copolymers such as that marketed under the trade designation "Poly bd CN-15" by Arco Chemical; polystyrene polymers such as that marketed under the trade designation "Styron 686" by Dow Chemical Co.; poly(-vinyl pyrrolidone) polymers such as those sold under the trade designation "K-30" (mol. wt 40,000) and "K-90" (mol. wt 360,000) by GAF Corp. of New York, N.Y., silicone fluids like that sold under the trade designation "Dow Corning 200" by the Dow Corning Corp., Midland, Mich., poly(methyl vinyl ether and comaleic anhydride half ester) such as that marketed under the trade designation "Gantrez ES 225" by GAF Corp., and paraffin oil such as that marketed by Fisher Scientific Co. having a Saybolt viscosity of 335 to 350. Such paraffin oils have a molecular weight exceeding 1,000, and hence may be considered as oligomers or low molecular weight ethylene polymers. It will be understood that many other incompatible polymers know to the art may also be used as phase separation agents for inducing phase separation of the bioabsorbable polymer material in the practice of the invention. Blends of polymeric materials with assorted natural oils (e.g., safflower oil, corn oil, glycerides) may also be used for phase separation.

In order to assess the coacervation and wetting behavior of coacervates formed from a variety of phase separation agents without consuming an unreasonable amount of material, a procedure has been developed which enables one to ascertain the liquid nature of the coacervate, co-acervate volume and composition, the effect of temperature on these factors and the ability of the coacervate to wet a given drug materials.

The procedure is as follows:

1. To 3-4 g. of a 2-3 wt.% solution of a bioabsorbable polymer in a 12 ml. graduated centrifuge tube, a solution of a phase-separation inducing agent is added dropwise with shaking. When the mixture becomes turbid and remains turbid on shaking, the weight of the phase inducer solution added is recorded along with the total volume of the solution.

2. After the two phases separate, the volume and consistency (liquid, gel-like or solid) of the coacervate phase are noted. If desired, increasing amounts of phase inducer solution may be added and the variation of coacervate volume and consistency with the amount of phase inducer solution added can be obtained.

3. To establish the effect of temperature upon coacervation, the centrifuge tubes from steps 1 and 2 above are equilibrated in a 100° C. water bath. In this manner, the nature and volume of the coacervate phase is evaluated at the boiling point of the solvent used or at 100° C., whichever is lower. This experment is also repeated at a temperature of +4° C.

4. The ability of a given coacervate to wet particles of a solid, injectable drug material is examined by using glass microscope culture slides with or without a polyethylene coating. These slides have a relatively deep cylindrical depression which retards solvent evaporation. The drug material is first placed in the depression of the slide and covered with supernatant solution from a coacervate system. A few drops of coacervate are then transferred to the depression by a syringe and the whole mixture stirred with a wire. The slide is then examined by a low power microscope to determine if the coacervate engulfs or wets or wraps the particles of the drug material. A visual measure of wetting quality is made and recorded.

5. Coacervate compositions are obtained by sampling coacervates with a 1 ml. syringe equipped with a flat needle. The syringe is weighed on an analytical balance and discharged into excess volatile nonsolvent for the bioabsorbable polymer material employed as the capsule wall material. This nonsolvent remains a solvent for the phase separation inducer. The precipitated bioabsorbable polymer forms a single lump which is removed from the system. It is vacuum dried along with the solvent/nonsolvent mixture which still contains the phase separation inducer thereby giving one the dried weight of bioabsorbable polymer capsule wall material and phase separation inducer in a known volume of coacervate. The composition of the coacervate is then readily calculated.

The above procedure was carried out using tartaric acid and cyclazocine as the materials to be encapsulated, dl-poly(lactic acid) bioabsorbable polymer material, toluene as the solvent, and a variety of phase separation inducers. The results obtained are shown in Table V.

TABLE V

Effect of Phase Inducers on dl-PLA Coacervate Formation in Toluene*

| Phase Inducer | Phase Inducer Conc., wt. % | PLA Conc., wt. % | Consistency 4° C. | Consistency 25° C. | Consistency 100° C. | Coacervate Phase Vol., % of total Volume | Coacervate Phase PLA content wt. % | Coacervate Phase Phase Inducer content, wt. % | Wetting Behavior Cyclazocine glass | Wetting Behavior Cyclazocine polyethylene | Wetting Behavior Tartaric acid, glass |
|---|---|---|---|---|---|---|---|---|---|---|---|
| 1. Low M.W. oils | | | | | | | | | | | |
| Castor oil | 16 | 2.7 | Gel | Gel | Liq. | 6 | — | — | — | — | — |
| Cottonseed Oil | 10.8 | 1.4 | — | Gel | — | 4.5 | — | — | — | — | — |
| Paraffin oil | 7.8 | 1.9 | Gel | Liq. | — | 7.2 | 14.8 | 4.9 | yes | — | — |
| Poly (ethylene glycol monoleate) | 20 | 2.5 | None | None | None | — | — | — | — | — | — |
| Safflower oil | 9 | 2.9 | Gel | Gel | Liq. | 5.8 | — | — | — | — | — |
| 2. Liquid Prepolymers | | | | | | | | | | | |
| Polybutadiene (Lithene PH) | 9.5 | 1.6 | Liq. | Liq. | — | 10.7 | 15.2 | 1.1 | no | yes | — |
| Poly (butadiene/alpha-methyl styrene (Lithene YH) | 6.2 | 2.9 | — | Gel. | — | 6.5 | — | — | — | — | — |
| Polybutadiene (Ricon 150) | 6.0 | 2.8 | — | Liq. | — | 15.0 | — | — | no | yes | yes |
| Polybutadiene (Butarez NF) | 6.0 | 3.0 | Liq. | Liq. | Liq. | 15.0 | 13.1 | 4.5 | yes | yes | — |
| Polybutadiene (Arco Polybd HT-45) | 6.0 | 2.8 | — | Liq. | — | 19.8 | — | — | no | yes | yes |
| Silicone oil (Dow Corning DC-200) | 3.0 | 3.0 | Liq. | Liq. | Liq. | 27.3 | 11.0 | — | no | — | — |
| 3. Polymers | | | | | | | | | | | |
| Polystyrene (Styron 686) | 3.8 | 2.5 | Liq. | Liq. | Liq. | 27.5 | — | — | no | — | — |
| Polybutadiene, (Ameripol 220) | 1.3 | 2.7 | Liq. | Liq. | — | 37.4 | — | — | no | — | — |
| Polyisobutylene (Butyl LM 430) | 8.0 | 1.9 | — | Liq. | — | 12.5 | 10.8 | 0.7 | no | — | — |

*The dl-PLA has an inherent viscosity of .819 at 30° C. in Benzene (1 wt. % solution)

As can be seen from Table V, most of the phase inducers or phase separation agents employed caused coacervation of the dl-poly(lactic acid) polymer in toluene at the concentration level noted. It can further be seen that oils like castor or safflower oil tend to give highly viscous or gel-like coacervates at 25° C. while the liquid prepolymers (including paraffin oil) and high molecular weight polymers produce primarily liquid coacervates at 25° C. Coacervates formed by the liquid prepolymer (except paraffin oil) and high molecular weight polymers remain liquidus below room temperature.

The consistency of a dl-poly(lactic acid) coacervate appears to be inversely related to its volume. In the case of this particular bioabsorbable polymer, where the coacervate occupies less than 6 to 8% of the total volume, its consistency is that of a gel. If it occupies more than 8% of the total volume, it is a liquid. As can be seen from the second column of Table V, the amount of phase inducer required to obtain phase separation varies widely.

Table VI shows some properties of dl-poly(lactic acid) coacervates formed in a 60/40 (W/W) acetone/e- thanol solvent system. The results show that in this solvent system, more of the coacervates appear to be liquid than in the case of the toluene systems. This may be due to the generally lower dl-poly(lactic acid) concentrations in the acetone/ethanol systems and/or higher solubility of dl-PLA in an acetone/ethanol mixture.

TABLE VI

Effect of Phase Inducers on dl-PLA Coacervate Formation in 60/40 Acetone/Ethanol (W/W)*

| Phase Inducer | Phase Inducer Conc. wt. % | PLA Conc., wt. % | COACERVATE PHASE | | | |
|---|---|---|---|---|---|---|
| | | | Consistency (25° C.) | Vol., % of total volume | PLA content wt. % | Phase Inducer Content, wt. % |
| Poly (ethylene glycol) (400 M.W.) | 11.4 | 1.0 | None | — | — | — |
| Poly (ethylene glycol) (600 M.W.) | 55 | 1.1 | None | — | — | — |
| Castor oil | 18 | 2.0 | Gel | 6.8 | — | — |
| Poly (methyl vinyl ether co-maleic anhydride half ester) | 9 | 1.1 Liq. | 4.1 | 19.8 | 2.2 | |
| Poly vinyl pyrrolidone (40,000 M.W.) | 11.3 | 1.0 | Liq. | 3.5 | 14.5 | 2.5 |
| Poly (vinyl pyrrolidone) (40,000 M.W.) | 11.1 | 2.1 | Liq. | 10.1 | | — |
| Poly (vinyl pyrrolidone) (360,000 M.W.) | 11.2 | 1.0 | Liq. | 3.5 | 7.9 | 2.8 |

*The dl-PLA has an inherent viscosity of .819 in benzene at 30° C. (1 wt. % solution)

The last three columns of Table V indicate the ability of dl-poly(lactic acid) coacervates to wet solid particles of cyclazocine and tartaric acid, the comments made being based upon microscopical evaluation of coacervate wetting behavior. The results shown indicate that the dl-poly(lactic acid) coacervate rarely wets cyclazocine when a relatively large glass surface area is available to compete for dl-poly(lactic acid) adsorption. However, when the glass surface has been coated with a material of low surface free energy (e.g., like polyethylene), cyclazocine is consistently wetted by dl-poly(lactic acid) coacervates obtained with liquid polybutadiene phase inducers. Tartaric acid was wetted by a dl-poly(lactic acid) coacervate even in the presence of glass. This may be due to the more polar nature of tartaric acid relative to cyclazocine.

It will be appreciated that similar data may be developed for various systems using other drug materials, bioabsorbable polymer materials, phase separation agents and solvents.

Phase separation of the bioabsorbable polymer is induced by the phase separation agent causing the phase separation at either room temperature or the reduced temperatures previously mentioned. The formation of a second phase occurs when its volume percent of the total volume of the system is less than approximately 10%. The addition of the phase separation agent produces a liquid coacervate which has an initial viscosity of less than approximately 1,000 centistokes and which wets and coats the particles of the solid, injectable drug material. The liquid coacervate capsule wall material must then be hardened or solidified in order to permit isolation of the microcapsules of the drug material thus formed. This is accomplished through the addition to the system of a nonsolvent for the bioabsorbable polymer material with a reduction in the temperature of the system to at least −30° C. as previously discussed. Such reduced temperatures favor reduced solubility of the polymer and increased viscosity of the coacervate phase being solidified and assist in avoiding agglomeration. Prior to the addition of the nonsolvent, the liquid wall of the microcapsules is a concentrated solution of the bioabsorbable polymer. The addition of the nonsolvent precipitates bioabsorbable polymer in the coacervate phase and promotes hardening or solidification of the liquid capsule wall.

As the nonsolvent, one may use any material in which the bioabsorbable polymer material is insoluble and which is miscible with the continuous phase of the system. It is highly preferred that the nonsolvent be relatively volatile so that the microcapsules may be readily dried by evaporation or volatilization of the nonsolvent. Illustrative nonsolvents useful in the practice of the invention include alkanes such as n-heptane, hexane and octane, fluorinated hydrocarbon solvents such as trichloromonofluoromethane, dichlorodifluoromethane, monochlorotrifluoroethane, carbon tetrafluoride, dichloromonofluoromethane, monochlorodifluoromethane, tetrachlorodifluoroethane, trichlorotrifluoroethane and dichlorotetrafluoroethane, all sold under the "Freon" trade designation by Du pont, Hydrogenated naphthalenes such as decahydronaphthalene and 1,2,3,4-tetrahydronaphthalene as well as mineral sprits or kerosene could also be used. Various other nonsolvents for the bioabsorbable polymer material may also be used in lieu of the above materials.

It has also been found that the rate of nonsolvent addition to the system may influence the permeability characteristics of the microcapsules obtained through the practice of the invention. Thus, a slower rate of addition of the nonsolvent, especially during the initial stages of nonsolvent addition, promotes better hardening or solidification of the liquid capsule wall and yields microcapsules which are more highly impermeable and which possess a more desirably defect free-wall membrane. After the nonsolvent addition to the system and the hardening of the liquid coacervate wall material, the nonsolvent is removed from the system by volatilization and the microcapsules produced are desirably washed with additional amounts of the nonsolvent and dried as by air drying or vacuum drying.

In order to avoid aggregation or agglomeration of the microcapsules formed by the method of the invention, it is essential to maintain the system in an agitated condition, as by means of mechanical stirring, throughout the practice of the method until such time as the microcapsule walls are solidified or partially solidified through the addition of the nonsolvent. This is particularly important for obtaining a satisfactory yield of microcapsules which are less than 300 microns ($\mu$) in size, i.e., microcapsules which pass a rectangular screen opening of 300μ on a side. In general, approximately 50% or more of the microcapsules obtained through the practice of the invention pass a 300μ screen opening. For example, using a 3-bladed polyethylene coated stirrer in a 300 ml. polypropylene or polyethylene centrifuge tube, we have found that a stirrer speed of between 100 rpm and 224 rpm gives a high yield of microcapsules below 300 microns in size.

The proportion of drug material to bioabsorbable polymer material may be varied widely and may range, for example, from a ratio of 1:5 or 1:1 to 10 or 20:1 (drug material to polymer). A typical useful proportion is 2 parts drug material to 1 part polymer material.

The novel microcapsules of the invention being less than 300 microns in size, are suitable for direct injection using conventional means, i.e., they are adapted to intramuscular or subcutaneous injection using 18 to 22 gauge needles. The microcapsules are suspended in a nonaqueous medium (e.g., peanut oil or sesame seed oil) or in an aqueous suspending medium, such as a 0.1–1.0% aqueous solution of methyl cellulose (pharmaceutical grade) or poly vinyl pyrrolidone, prior to injection. Aluminum monostearate (2 wt. %) may be added to the oils. Thus injected, the microcapsules permit controlled or sustained time release of the encapsulated drug material over an extended period with no physiologically adverse effects being caused by the bioabsorbable polymer wall material at the time of injection or thereafter.

It will be apparent to those skilled in the art that the drug material employed should have a starting particle size of less than 300 microns and preferably below 200 microns. If the drug material has a greater particle size, it can be subjected to conventional mechanical reduction procedures to bring its size within the desired size level.

In still another aspect of the invention, it has been found that the humidity of the environment to which the drug and bioabsorbable polymer material are exposed before, during and after the microencapsulation is carried out may have an important effect on the nature of the microcapsules formed. For example, hydrophobic drugs such as naltrexone pamoate and other narcotic antagonists, should be equilibrated in a humid environment before encapsulation is carried out. Such equilibration provides drug particles saturated with adsorbed water ic coating thereby yielding capsules that release their drug payload slowly. The drug may be equilibrated prior to microencapsulation as by being conditioned for 3 to 7 days in a dessicator the bottom of which is covered with liquid water.

With hygroscopic or hydrophilic drugs such as various synthetic polypeptides on the other hand, it becomes necessary to restrict the access of moisture to the drug before and during microencapsulation. This may be accomplished by thoroughly drying the drug before microencapsulation, keeping exposure to humid environments to a minimum before microencapsulation and severely restricting contact of moisture with the drug during the encapsulation process as by using a nitrogen purge and cover over the capsule reactor. Further, moisture in contact with the drug can be reduced by keeping the reactor temperature at or near room temperature during the phase separation step and then cooling the system to the reduced temperatures previously stated during the isolation step. After the microcapsules walls have solidified and the microcapsules are isolated, the reactor and its contents may be warmed to 25° C. before the nitrogen purge and cover are removed. Thus, maintaining the capsule reactor and contents cold when encapsulating a hygroscopic drug material is undesirable unless the moisture entering the reactor is kept at a minimum. Ideally, for hygroscopic or hydrophilic drugs such as polypeptides, atmospheric conditions of low relative humidity (e.g., 20–30% RH at 75° F.) are desirable.

The following examples illustrate the invention:

EXAMPLE 1 dl-Poly(lactic acid) polymer (1 g.) having an inherent viscosity of 0.819 in benzene at 30° C. (1 wt. % solution) was dissolved in toluene (50 ml.) and the resulting solution placed in a 250 ml. glass beaker. The solution was kept at room temperature and tartaric acid (3 g.) was added to the solution with mechanical stirring using a metal stirrer. A liquid butadiene polymer (sold under the trade designation "Poly bd R-45 HT" by Arco Chemical Company of Philadelphia, Pa.) was then added incrementally (total of 20 ml. of a 50/50 V/V solution of the polymer in toluene) to the stirred mixture of tartaric acid and dl-poly(lactic acid) solution. This caused phase separation of the dl-poly(lactic acid) from the solution. The separated dl-poly(lactic acid) formed a liquid coacervate which wetted and engulfed the individual tartaric acid particles. After this step, the system was cooled in a dry ice/isopropanol bath. A total of 125 ml. of n-heptane (also cooled to dry ice/isopropanol temperature) was then added to the system, after which stirring was discontinued. The microcapsules which had formed were allowed to settle and the solution decanted. The microcapsules were washed four to five times with n-heptane and isolated by air drying at room temperature on filter paper.

EXAMPLE 2 dl-Poly(lactic acid) polymer (1 g.) having an inherent viscosity of 0.819 in benzene at 30° C. (1 wt % concentration) was dissolved in toluene (50 ml.) in a polyethylene beaker equipped with a polyethylene coated stirrer. Cyclazocine free base (3 g.) was added with mechanical stirring to this solution. A liquid polybutadiene (marketed under the trade designation "Lithene PH" By Lithium Corp. of America; 25 ml. of a 25% V/V solution of the liquid polybutadiene in toluene) was then added to the stirred solution. The system had been maintained at room temperature through this step, and the addition of the liquid polybutadiene caused phase separation of the dl-poly(lactic acid) from the solution. This formed a liquid coacervate which wetted and engulfed the discrete cyclazocine particles. The entire system was then cooled to a dry ice/isopropanol temperature and similarly cooled n-heptane (150 ml.) was added dropwise. Stirring was discontinued and the discrete microcapsules which had formed were washed four times with n-heptane. The microcapsules were then isolated by air drying at room temperature on filter paper.

Of the isolated cyclazocine microcapsules, approximately 50% by weight were <295μ in size (i.e., passed a rectangular screen opening of 295μ on a side). Microcapsules of such size were readily suspended in water containing 0.19% by weight of a suspending medium (marketed under the trade designation "Methocel" by Dow Chemical Co.) and the resulting suspension ejected completely from a standard 18 gauge needle.

Approximately 14% of the capsules obtained were retained by a 595μ rectangular screen opening and approximately 33% passed by a 595μ opening and were retained by a 295μ opening.

EXAMPLE 3

Example 2 was repeated except that the encapsulation procedure was carried out in a glass beaker and a metal stirrer was employed.

The microcapsules isolated had the following sieve analysis:

| | |
|---|---|
| Retained by 595μ rectangular screen opening (>595μ) | 4% |
| Passed by 595μ opening and retained by 295μ opening | 20% |
| Passed by 295μ opening (<295μ) | 59% |

The microcapsules obtained in Examples 2 and 3 were then subjected to the following procedure to determine the relative rate of release of cyclazocine therefrom.

15 mg. each of the respective microcapsules were placed in each of 8 to 10 glass bottles, each measuring approximately 140 mm.×30 mm.×2.5 mm. phosphate buffer (75 ml.) consisting of equal parts of 0.1M HCl and 0.1M KH$_2$PO$_4$ adjusted to respective pH values of 7.4 and 7.0 with 10N sodium hydroxide, was added. The bottles were rotated in a water bath at 37° C. at the rate of 40 revolutions/min. At the respective intervals (e.g., 0.5 hrs., 1 hr., 3 hrs., 5 hrs., etc.) a 5 ml. sample is removed, placed in a cuvette and the absorbance run (e.g., absorbance run at wavelength 278 fo cyclazocine on a Beckmann DK-1 spectrophotometer) for determining the amount of cyclazocine leached from the sample. The sample was then discarded and a fresh sample used for each reading.

The following release data were obtained by this end-over-end tumbling procedure at 37° C. in the buffer solution adjusted to pH 7.0 using microcapsules less than 295μ in size.

| | Release of cyclazocine % | |
|---|---|---|
| Extraction time, hrs. | Capsules from Example 2 | Capsules from Example 3 |
| .6 | 15% | 33% |
| 2.3 | 57% | 59% |
| 3.3 | 59% | 72% |
| 24 | 97% | 85% |

It will be observed that the microcapsules prepared in a polyethylene container generally appeared to release cyclazocine more slowly than microcapsules made in a glass beaker. Unencapsulated cyclazocine is completely dissolved in the same buffer solution within 15 minutes.

EXAMPLE 4

Example 2 was repeated except that the drug material encapsulated was a narcotic antagonist known under the trade designation "Naltrexone" (free base form) (Endo Laboratories). "Naltrexone" (3 g.) and dl-poly(-lactic acid) (1 g.) with an inherent viscosity of 0.819 (30° C.; benzene; 1 wt. %). The isolated capsules had the following sieve analysis:

| Rectangular Screen Opening | Wt. Capsules g. | % of Capsules isolated | "Naltrexone" Content |
|---|---|---|---|
| Retained on 595μ | 0.57 | 19.5 | — |
| Passed 595μ; retained by 295μ | 0.39 | 13.4 | 68.3 |
| Passed 295μ; retained by 177μ | 0.61 | 20.9 | 67.0 |
| Passed 177μ; retained by 105μ | 0.76 | 26.0 | 65.3 |
| Passed 105μ | 0.59 | 20.0 | — |
| Total wt. isolated | 2.92 g. | 100.0 | |

Theoretical max. wt. isolated 4.00 g.
Actual capsule yield ≈ 73%

It was found that the encapsulated "Naltrexone" released more slowly into a phosphate-saline buffer solution at pH 7.0 than did the unencapsulated drug material.

EXAMPLE 5

Cyclazocine (free base) (3 g.) was encapsulated with a system containing dl-poly(lactic acid) (1 g.) having an inherent viscosity of 0.717 (1 wt. % conc.; 30° C.; benzene as solvent) dissolved in toluene (50 ml.) to which a liquid polybutadiene phase inducer (20 ml. of 25 vol. % solution of liquid polybutadiene marketed under the trade designation "Lithene PH" in toluene) was added. The system was continuously agitated. The capsules were made in a polyethylene container using a polyethylene-coated stirrer. n-Heptane was used to isolate the capsules as described in the previous examples. The capsules formed were isolated by cooling them to 0°–5° C. with a water/ice bath and adding to them at this temperature excess n-heptane which had been cooled to −18° C. The capsules isolated had the following sieve analysis:

| Rectangular Screen Opening | Wt. Capsules g. | % Capsules isolated |
|---|---|---|
| >595μ | 0.074 | 2.12 |
| <595μ | 0.804 | 23.04 |
| <295μ; >177μ | 1.58 | 25.27 |
| <177μ; >105μ | 0.70 | 19.97 |
| <105μ | 0.34 | 9.60 |
| Total wt. isolated | 3.498 | 100.0% |

Theoretical total wt. = 4.00
Actual capsule yield = 87.5% of theoretical

The release data obtained by following the above-noted release procedure for microcapsules less than 295μ are as follows:

| Extraction time hrs. | Cyclazocine Release, % |
|---|---|
| 0.5 | 22.4 |
| 3.0 | 60.4 |
| 5.0 | 84.4 |
| 24.0 | 100.0 |

The test was carried out at 37° C. with the buffer solution at pH 7.4 prepared as described above. The unencapsulated cyclazocine was completely dissolved within 15 minutes of extraction.

EXAMPLE 6

Example 5 was repeated except that the n-heptane used to isolate the capsules was added dropwise (120 drops/min.) whereas in Example 5 it was added in a steady stream (i.e., poured into the container in a matter of seconds). The total volume of n-heptane added in all examples is at least 150 ml., but dropwise addition substantially lengthens the time required to isolate the capsules.

The sieve analysis of the capsules obtained is as follows:

| Rectangular Screen Opening | Wt. Capsules g. | % Capsules isolated |
|---|---|---|
| >595μ | 0.20 | 5.39 |
| <595μ; >295μ | 0.51 | 13.67 |
| <295μ; >177μ | 1.48 | 39.6 |
| <177μ; >105μ | 0.91 | 24.4 |
| <105μ | 0.63 | 16.9 |
| Total wt. isolated | 3.73 | 99.96 |

Theoretical total wt. = 4.00
Actual capsule yield = 93.2% of theoretical

Thus, dropwise addition of the nonsolvent gives somewhat more capsules passing a 295μ screen opening.

A comparison was made of the release rate or ratio of extraction of cyclazocine from capsules made in Example 5 with those in Example 6 at 37° C. in a phosphate/saline buffer kept at pH 7.4 (prepared as described above), the capsules in both cases being those passing a 295 screen opening and retained by a 177 screen opening. The results are as follows:

| Extraction time hrs. | Example 6 capsules | Example 5 capsules |
|---|---|---|
| .5 | 11.7 | 22.4 |
| 3.0 | 35.9 | 60.4 |
| 5.0 | 52.5 | 84.4 |
| 24.0 | 95.0 | 100 |

Thus, the slower rate of addition of the nonsolvent reduces the tendency for the capsule walls to precipitate and improves the wall morphology favoring retention of the drug material by the capsules.

EXAMPLE 7

Example 6 was repeated except that the bioabsorbable polymer used was a copolymer of lactic acid (90 wt. %) and glycolic acid (10 wt. %) and the phase inducer was 20 ml. of a 50 vol. % solution of a liquid polybutadiene polymer marketed under the trade designation "Lithene PH" in toluene. The capsules were isolated by dropwise addition of n-heptane into the system as described in Example 6. The sieve analysis of the capsules obtained was as follows:

| Rectangular Screen Opening | Wt. Capsules g. | % Capsules isolated |
|---|---|---|
| >595μ | 1.234 | 32.6 |
| <595μ; >295μ | 2.530 | 66.8 |
| <295μ; >177μ | 0.023 | 0.6 |
| <177μ | trace | — |
| Total wt. isolated | 3.787 | 100.0 |

Theoretical total wt. = 4.00
Actual capsule yield = 94.6% of theoretical

The above data indicate that capsules can be made with a glycolide/lactide copolymer although the yield of capsules less than 295μ in size is small.

EXAMPLE 8

Example 7 was repeated using a copolymer of lactic acid (80 wt. %) and glycolic acid (20 wt. %) (1 g.) dissolved in benzene (50 ml.) at 25° C. Cyclazocine free base (3 g.) was suspended in this solution contained in a polyethylene container and stirring was carried out with a polyethylene-coated stirrer. To the suspension was added a liquid polybutadiene polymer marketed under the trade designation "Lithene PH" (20 ml. of 20% by vol. solution in benzene). The system was maintained at room temperature and n-heptane (also at room temperature) was added dropwise. When the n-heptane addition had been completed and stirring was stopped, a single large mass of material was obtained and upon vacuum drying for 4 days at 25° C., this broke up into capsules having the following sieve analysis:

| Rectangular Screen Opening | Wt. Capsules g. | % Capsules isolated |
|---|---|---|
| >595μ | 0.017 | 0.5 |
| <595μ; >295μ | 1.300 | 40.5 |
| <295μ; >177μ | 1.359 | 42.3 |
| <177μl >105μ | 0.461 | 14.4 |
| <105μ | 0.073 | 2.3 |
| Total wt. isolated | 3.210 | 100.0 |

Theoretical total wt. = 4.00
Actual capsule yield = 80.3% of theoretical

To demonstrate the slower release properties of the capsules (<295 and >177μ in size) relative to unencapsulated cyclazocine, the above-described release test 14 procedure was followed using phosphate-saline buffer at pH 7.4 and 37° C. The following results were obtained.

| Extraction time hrs. | Cyclazocine Release, % |
|---|---|
| 0.5 | 10.6 |
| 3.0 | 41.6 |
| 5.0 | 83.2 |
| 24.0 | 91.2 |

EXAMPLE 9 dl-Poly(lactic acid) polymer (1 g.) having an inherent viscosity at 30° C. in benzene (1 wt. % conc.) of 0.717 was dissolved in toluene (50 ml.) in a polyethylene container. Cyclazocine free base (3 g.) was added to this solution at room temperature and the system stirred with a polyethylene-coated stirrer. To one sample of the system was added 20 ml. of a 25 vol. % solution of "Lithene PH" in toluene followed by the addition of 5 ml. of a 20 vol. % solution of "Lithene PH" in toluene. To a second sample of the system was added 30 ml. of a 25 vol. % solution of "Lithene PH" in toluene. Both samples were then cooled to dry ice/isopropanol temperature and n-heptane precooled to −18° C. was added dropwise (120 drops/min.). Upon completion of the n-heptane addition (approx. 150 ml.) sitrring was discontinued. In both cases, microcapsules were isolated, a portion of which were less than 295μ in size.

EXAMPLE 10

A solution was prepared at room temperature containing 80 wt. % lactide/20 wt. % glycolide copolymer (1 g.) in benzene (50 ml.) in a polyethylene container. Antimony potassium tartrate (3 g.) was added to the solution and the system stirred with a polyethylene-coated stirrer. To the system was then added 30 ml. of a 20 vol. % solution of "Lithene PH" in benzene. The agitated system was cooled to 0°-5° C. with a water/ice bath and n-heptane (precooled to −18° C.) was added dropwise (120 drop/min.). When the n-heptane addition (approx. 150 ml.) was completed, stirring was discontinued and the capsules were washed with excess n-heptane and dried. A portion of the isolated microcapsules were less than 295μ in size.

EXAMPLE 11

A solution was prepared at room temperature containing a dl-poly(lactic acid) polymer (1 g.) having an inherent viscosity of 1.13 in benzene at 30° C. (1 wt. % solution) in toluene (50 ml.) in a polyethylene container. Digitoxin (1 g.) was added to the solution and the system stirred with a polyethylene-coated stirrer. To the system was added 30 ml. of a 20 vol. % solution of "Lithene PH" in toluene. The agitated system was cooled to dry ice/isopropanol temperature and n-heptane (precooled to −18° C.) was added dropwise (120 drops/min.). When the n-heptane addition (approx. 150 ml.) was completed, stirring was discontinued and the capsules were washed with excess n-heptane and dried. A portion of the dry, free-flowing microcapsules obtained were less than 295 in size.

EXAMPLE 12

A solution was prepared at room temperature by dissolving 1 g. of dl-poly(lactic acid) polymer (1 g.) having an inherent viscosity of 1.02 in benzene at 30° C. (wt. % solution) in toluene (50 ml.) in a polyethylene container. An alcohol-sensitizing agent, citrated calcium cyanamide (3 g.), was added to the solution and the system stirred with a polyethylene-coated stirrer. To the system was added 30 ml. of a 25 vol. % solution of "Lithene PH" in toluene to induce phase separation of the dl-poly(lactic acid) polymer. The agitated system was cooled to dry ice/isopropanol temperature and n-heptane (precooled to −18° C.) was added dropwise (60 drops/min.). Upon completion of the n-heptane addition (approx. 150 ml.), stirring was discontinued and the capsules were washed with excess n-heptane and dried. A portion of the dry microcapsules obtained were less than 295μ in size.

EXAMPLE 13

Example 12 was repeated except that the drug material was tetracycline, a representative antibiotic, and 20 ml. of a 25 vol. % solution of "Lithene PH" in toluene was employed as the phase separation inducer. Dry, free-flowing microcapsules were isolated, a portion of which were less than 295μ in size.

EXAMPLE 14

Example 12 was repeated except that the drug material was ethisterone, a representative birth control agent, and 15 ml. of a 25 vol. % solution of "Lithene PH" in toluene was employed as the as the phase separation inducer. Dry, free-flowing microcapsules were isolated, a portion of which were less than 295μ in size.

EXAMPLE 15

A solution was prepared at room temperature by dissolving 2 g. of dl-poly(lactic acid) polymer with an inherent viscosity (1 wt. % solution in benzene at 30° C.) of 1.02 in 50 ml. of toluene in a polyethylene container. Cyclazocine (6 g.) was added to the solution and the system stirred with a polyethylene-coated stirrer. To the system was added 20 ml. of a 25 vol. % solution of "Lithene PH" in toluene to induce phase separation of the polymer. The agitated system was cooled to dry ice/isopropanol temperature and n-heptane (precooled to −18° C.) was added dropwise (60 drops/min.). Upon completion of the n-heptane addition (approx. 150 ml.), stirring was discontinued and the capsules were washed with excess n-heptane and dried. A portion of the dry microcapsules obtained were less than 295μ in size.

The sieve analysis of the capsules obtained was as follows:

| Rectangular Screen Opening | Wt. Capsules g. | % Capsules isolated |
| --- | --- | --- |
| >595μ | 0.787 | 13.66 |
| <595μ; >295μ | 1.360 | 23.61 |
| <295μ; >177μ | 2.275 | 39.50 |
| <177μl >105μ | 1.050 | 18.23 |
| <105μ | 0.288 | 5.00 |
| Total wt. isolated | 5.760 g. | 100.00 |

Theoretical total wt. = 8.00 g.
Actual capsule yield = 72% of theoretical

To demonstrate the slower release properties of the capsules (105μ to 177μ fraction) relative to unencapsulated cyclazocine, the above-described release test procedure was followed using phosphate-saline buffer at pH 7.4 and 37° C. The following results were obtained:

| Extraction time hrs. | Cyclazocine Release, % |
| --- | --- |
| 3 | 14.3 |
| 16 | 34.6 |
| 24 | 39.7 |
| 50 | 52.7 |
| 72 | 64.9 |

For in vivo release evaluation, microcapsules prepared above (between 105μ and 177μ in size) were suspended in a 0.1% aqueous solution of methyl cellulose and the resulting suspension injected into seven rats at a dosage rate of 30 mg. drug material/kg. body wt. After a known period, the rats were given a 15 mg. morphine/kg. body wt. challenge dose. If the narcotic antagonist (cyclazocine) injected was effective in blocking the effect of the morphine, the rats when placed on a heated hot-plate would require the normal response time of untreated rats to remove their paws. This value is 7-8 sec. If the cyclazocine injected is having no effect on the rats' response, the response time should be 30 sec. (i.e., the time found for control rats who have been given 15 mg. morphine/kg. body wt. and no narcotic antagonist to respond to the hot plate test). The following results were obtained:

| Time after injection, days | Response time to hot plate test, secs- |
| --- | --- |
| 1 | 12 sec. |

| Time after injection, days | Response time to hot plate test, secs |
|---|---|
| 2 | 5 sec. |
| 3 | 9 sec. |
| Control (no cyclazocine) | 30–22 sec. |

The data demonstrate clearly that sustained release of the cyclazocine is provided by the microcapsules. Also, none of the rats injected with cyclazocine microcapsules (30 mg. drug/kg. body wt.) showed any evidence of toxic effects (e.g., loss of motor control, etc.). A dose of 2.5 mg. unencapsulated cyclazocine/kg. body wt. causes very obvious and severe toxic effects. The dose of cyclazocine microcapsules was more than ten times greater than that needed for toxic effects to appear thus providing clear evidence of slow release.

The test was discontinued after three days because the rats in the control group showed some sign of becoming accustomed to the morphine dose used to challenge the rats.

EXAMPLE 16

A solution containing 1 g. of a dl-poly(lactic acid) polymer (inherent viscosity of 1.02 at 30° C. in benzene and concentration of 1.0 wt. %) in 50 ml. of toluene was prepared in a polyethylene container. Naltrexone Pamoate, a narcotic antagonist (Endo Laboratories), (0.8 g.) was added to the solution and the system stirred with a polyethylene-coated stirrer. To the system was added 15 ml. of a 25 vol. % solution of "Lithene PH" in toluene. The agitated system was cooled to dry ice-isopropanol temperature and n-heptane (precooled to −18° C.) was added dropwise (60 drops/min.). Upon completion of the n-heptane addition (approx. 150 ml.), stirring was discontinued and the capsules were washed with excess n-heptane and dried. Dry, free-flowing microcapsules were obtained, a portion of which were less than 295$\mu$ in size and which had a half-life greater than 5–8 hrs. when tested according to the release procedure previously described.

EXAMPLE 17

Cyclazocine was encapsulated with two different bioabsorbable polymers.

80 wt. % lactic acid/20 wt. % glycolic acid copolymer (80/20 lactide/glycolide copolymer) (1 g.) was dissolved in benzene (50 ml.) and to this solution in a polyethylene container was added cyclazocine (3 g.) at 25° C. The system was stirred with a polyethylene-coated stirrer. To the system was added 30 ml. of a 25 vol. % solution of "Lithene PH" in benzene. The 80/20 lactide/glycolide coacervate phase that formed engulfed the particles of cyclazocine and was then solidified by the addition of n-heptane (at approximately +10° C.) at a rate of 60 drops/min.

The thus coated cyclazocine particles were isolated by filtration and then placed in toluene (50 ml.) containing a dl-poly(lactic acid) polymer (2 g.) having an inherent viscosity of 1.02 (1 wt. % conc) in benzene at 30° C. Phase separation was induced by the addition of 20 ml. of a 25 vol. % solution of "Lithene PH" in toluene. The agitated system was cooled to dry ice/isopropanol temperature and n-heptane was added dropwise (60 drops/min.) to solidify the outer coating of dl-poly(lactic acid) polymer. Stirring was discontinued and the capsules were isolated and dried.

A two polymer coating is obtained because the 80/20 lactide/glycolide copolymer is insoluble in toluene and soluble in benzene. Thus, when it was deposited from benzene on the cyclazocine particles, it was not dissolved off when the toluene solution of dl-poly(lactic acid) was added.

A total of 4.5 g. of microcapsules was isolated from the above procedure and, of this total, 1 g. was <295$\mu$ in diameter (or passed 295$\mu$ rectangular screen opening).

The fraction of capsules lying between 177$\mu$ and 295 contained 50.3 wt.% cyclazocine and released cyclazocine at 37° C. in pH 7.4 phosphate buffer at the following rate:

| Extraction time hrs. | % Drug in Capsules extracted |
|---|---|
| 1 | 16.4 |
| 7 | 38.3 |
| 17 | 57.7 |
| 24 | 62.2 |
| 48 | 77.1 |

The two polymer wall coatings vary in the rate at which they undergo bioabsorption, i.e., the glycolide/lactide copolymer undergoes absorption more rapidly than the poly(lactic acid) polymer.

EXAMPLE 18

Cyclazocine was encapsulated using a mixture of benzene and xylene as the solvent system.

A solution was prepared at room temperature containing a dl-poly(lactic acid) polymer (2 g.) in xylene (54 ml.) in a polyethylene container. Cyclazocine (3 g.) was suspended in this solution and benzene (25 ml.) was added. The system was stirred with a polyethylene-coated stirrer. To the system was added 34 ml. of 20 vol. % solution of "Lithene PH" in benzene to cause phase separation of the dl-poly(lactic acid) polymer. The system was then chilled to −18° C. and n-heptane was added dropwise (60 drops/min.). After the n-heptane addition, stirring was discontinued and the capsules were washed with excess n-heptane and dried. Dry, free-flowing microcapsules were obtained, a portion of which where less than 295$\mu$ in size.

EXAMPLE 19

The procedure set forth in col. 10, lines 48 to 56 of U.S. Pat. No. 3,773,919 was followed in an effort to produce microcapsules. Thus, drug particles were suspended in a chloroform solution of dl-poly(lactic acid) polymer in a covered glass beaker equipped with a motor driven 2-bladed stainless-steel stirrer. Hexane was added slowly (at the rates given in Table VII). In every run, it was observed that the solution remained homogeneous (except for the presence of the drug particles) as hexane is added until about 1.4 times the original volume of chloroform had been added. If one stopped adding hexane at that time, the polymer stuck together and no particles or microcapsules were obtained. If one continued adding hexane, gradually the polymer-rich phase became less sticky and products could be isolated. The products were filtered, washed with hexane on the filter paper and allowed to dry.

All runs were made with dl-poly(lactic) polymer having an inherent viscosity of 1.02 at a solution concentration of 1 wt. % in benzene at 30° C. In all cases, 100 ml. of a chloroform solution of the polymer was used.

Table VII summarizes the range of conditions examined and the products obtained. The three drug materials which were investigated were antimony potassium tartrate, a water soluble drug utilized in the treatment of schistosomiasis, 17-β-estradiol, a hormone soluble in ethanol and cyclozacine free base, a narcotic antagonist.

The weight ratio of drug of polylactide polymer was varied from 3:1 to 10:1. Only ratios greater than 7.6:1 gave individual particles but none of these constituted true microcapsules. Lower ratios gave large clumps or drug-polymer aggregates in the form of a film coated on the beaker wall, e.g., see comparison of the third and last column in Table VII.

Table VIII presents the size distributions from the batches listed in Table VII with corresponding run numbers given with those prepared by the procedure of U.S. Pat. No. 3,773,919 and compares them with microcapsules prepared in accordance with the present invention by the procedure set forth in Example 2 or a slight variation thereof which made no material affect on the results. As can be seen, the procedure based upon the aforementioned patent yields particles which tend to be larger than 295 microns in size, whereas with the process of the present invention, all but two runs produced microcapsules in a yield of over 70% by weight in the injectable range, i.e., smaller than 300 microns in size.

polymer particles which are much smaller than the original particle.

More specifically, the products of runs 6, 4 and 7 of Table VII (representing three different drugs, i.e., 17-62-estradiol, antimony potassium tartrate and cyclozacine) were extracted with absolute ethanol, water and 0.1 molar HCl, respectively. It was found that, considering particle sizes below 295 microns on a comparative basis, the products made according to the present invention remain as shells after extraction, having a size similar to the original microcapsules, whereas with the products prepared in accordance with U.S. Pat. No. 3,773,919, on the other hand, the products tended to be either smaller, as in the case of runs 6 and 4 of Table VII or net-like extended shreds as in the case of cyclozacine (run 7 from Table VII), all as shown from magnified microslides of the respective products. It is concluded, therefore, that the products made according to the present invention are true microcapsules while the products made in accordance with the procedure of U.S. Pat. No. 3,773,919 are drug-polymer aggregates.

Further, scanning electromicrographs of the products produced in accordance with U.S. Pat. No. 3,773,919 show that the drug is frequently on the outside of the drug-polymer aggregates with the polymer acting as a cement for the drug particles rather than as an envelope surrounding the drug particles.

EXAMPLE 20

Naltrexone pamoate (4 g.; 105 microns particle size) were dispersed at 25° C. in toluene (50 ml.) containing

TABLE VIII

| | Size Distribution | | | | | | | | | | |
|---|---|---|---|---|---|---|---|---|---|---|---|
| | Procedure Based on U.S. Pat. No. 3,773,919 | | | | Procedure Based on Present Invention | | | | | | |
| Run | 1 | 2 | 6 | 7 | 1 | 2 | 3 | 4 | 5 | 6 | 7 |
| Drug | APT | APT | BEST | CYCL | CYCL | BEST | Naltrexone | CYCL | APT | BEST | BEST |
| Wt. Drug/ wt. Polymer | 10.0 | 10.0 | 7.6 | 8.4 | 3.0 | 2.5 | 0.53 | 3.0 | 3.0 | 3.0 | 10.0 |
| Sieve Size Fraction (microns) | | | | | WEIGHT PERCENT | | | | | | |
| >595 | 83.44 | 82.64 | 80.18 | 71.6 | 13.19 | 49.5 | 10.94 | 6.91 | 10.2 | 10.7 | 6.6 |
| 295 to 595 | 16.37 | 9.43 | 6.83 | 10.3 | 15.00 | 29.2 | 9.25 | 19.37 | 1.5 | 11.2 | 49.4 |
| 177 to 295 | 0.19 | 6.04 | 3.79 | 10.3 | 54.86 | 11.80 | 18.64 | 56.80 | 4.8 | 20.7 | 33.9 |
| 105 to 177 | 0 | 0.76 | 5.49 | 5.7 | 15.56 | 6.42 | 42.91 | 15.13 | 42.1 | 27.9 | 8.9 |
| <105 | 0 | 1.13 | 3.71 | 2.1 | 1.39 | 3.06 | 18.26 | 2.11 | 41.4 | 29.5 | 1.2 |
| Percent Smaller Than 295 | 0.19 | 7.93 | 12.99 | 18.1 | 71.81 | 21.28 | 79.81 | 74.04 | 88.3 | 77.1 | 43.0 |

APT = Antimony potassium tartrate, K and K Laboratories
BEST = 17-β-estradiol, Sigma Chemical Company
CYCL = Cyclozacine, Sterling-Winthrop In addition, studies were made to determine the differences between the microcapsules produced in accordance with the present invention and the products made in accordance with the aforesaid procedure of U.S. Pat. No. 3,773,919. This was done by placing the products or microcapsules under the stage of an optical microscope on a slide which has a depression. When a sufficient amount of solvent for the drug material but nonsolvent for the polymer is added, the drug gradually dissolves leaving only the polymer particles. In the case of microcapsules prepared in accordance with the present invention, it was observed that the result was largely transparent skins or ghosts which have approximately the size and shape of the drug microcapsules they contained. On the other hand, particle aggregates prepared in accordance with U.S. Pat. No. 3,773,919 tend to yield dl-poly(lactic acid) polymer (2 g.; inherent viscosity of 0.717 in benzene at 30° C. (1 wt. % solution)). A solution (20 ml.) containing 25 vol. % liquid polybutadiene (marketed under the trade designation "Lithene PH") was then added and the temperature of the system cooled to −90° F. to −96° F. Normal heptane was then added to the system at the rate of approximately 10 drops/10 sec. until the system contained approximately 200 to 250 ml. of solution. The microcapsules which had formed were then decanted off, washed four times with fresh n-heptane and dried.

Microcapsules (177–295 microns in size) so prepared were evaluated by the mouse tail-flick test procedure. Mice (groups of 6) were the test animals. The morphine challenge dose was 10 mg./kg. mouse; test animal response was measured 20 min. after morphine injection. The results, reported as % antagonism are set forth in Table IX. As will be seen, the microcapsules caused more than 50% antagonism 28 days after injection both in the tests in which peanut oil was used as the suspending medium and in the tests where peanut oil plus aluminum monostearate was used as the suspending medium. It may also be noted that the microcapsules injected with peanut oil containing aluminum monostearate still showed 80% antagonism 28 days after injection.

TABLE IX

In Vivo Behavior of dl-PLA Naltrexone Pamoate Capsules Effect of Increased Dose and Aluminum Monostearate (AIMS)*

| Dose Administered | Suspending Medium | % MPE (maximum possible effect), days after injection | | | |
|---|---|---|---|---|---|
| | | 7 | 14 | 21 | 28 |
| Control | Peanut oil | 87.8 | 88.0 | 85.3 | 74.3 |
| | | % Antagonism, days after injection | | | |
| 40 mg unencapsulated NP/kg mouse | Peanut oil | 66.1 | 59.1 | 12.9 | 13.9 |
| 60 mg NP capsules/kg mouse | Peanut oil | 85.6 | 91.1 | 59.7 | 54.4 |
| | | % MPE, days after injection | | | |
| Control | Peanut oil + 2 wt. % AIMS | 96.6 | 99.0 | 89.3 | 83.8 |
| | | % Antagonism, days after injection | | | |
| 40 mg unencapsulated NP/kg mouse | Peanut oil + 2 wt. % AIMS | 88.3 | 52.9 | 11.2 | 18.4 |
| 60 mg NP capsules/kg mouse | Peanut oil + 2 wt. % AIMS | 79.5 | 91.9 | 61.5 | 80.8 |

*All injections (1 cc/100 g mouse) given through 18 gauge needle; Morphine challenge dose: 10 mg/kg mouse; Capsule size: 177–295µ; Active content of capsules initially: 67 wt. %.

Similar studies were run with microcapsules (105 to 177 microns in size) of naltrexone free base (NFB) prepared in the same manner as the naltrexone pamoate microcapsules. The results are set forth in Table X.

EXAMPLE 21

A series of encapsulation runs was conducted at different coacervation temperatures and different isolation temperatures.

The procedure involved dissolving 1.0 g. or 0.5 g. of di-poly(lactic acic) (dl-PLA) polymers of various molecular weights in 40 ml. of solvent and dispersing in this solution the internal phase or drug. The solvent employed was toluene except that one run was made with trichloroethylene. The various di-poly(lactic acid) polymers used are listed in Table XI.

TABLE X

In Vivo Behavior of dl-PLA Naltrexone Free Base (NFB) Capsules*

| Dose Administered | Suspending Medium | % MPE (maximum possible effect), days after injection | | | |
|---|---|---|---|---|---|
| | | 7 | 10 | 14 | 21 |
| Control | Peanut oil | 96.6 | 77.0 | 94.5 | 86.8 |
| | | % Antagonism, days after injection | | | |
| 40 mg unencapsulated NFB/kg mouse | Peanut oil | 80.0 | 39.7 | 21.8 | 8.1 |
| 60 mg NFB capsules/kg mouse | Peanut oil | 74.4 | 85.6 | 90.1 | 34.3 |
| | | % MPE, days after injection | | | |
| Control | Peanut oil + 2 wt. % aluminum monostearate (AIMS) | 95.0 | 88.8 | 100 | 93.0 |
| | | % Antagonism, days after injection | | | |
| 40 mg unencapsulated NFB/kg mouse | Peanut oil + 2 wt. % AIMS | 54.1 | 69.5 | 48.0 | 15.2 |
| 60 mg NFB capsules/kg mouse | Peanut oil + 2 wt. % AIMS | 75.6 | 93.0 | 96.0 | 56.0 |

*All injections (1 cc/100 g mouse) given through 18 gauge needle; Morphine challenge dose: 10 mg/kg mouse; Capsule size: 105–177µ; Active content of capsules initially: 67 wt. %.

TABLE XI

Characterization Data For dl-PLA Samples

| Sample Designation | Intrinsic Viscosity,** dl/g | Molecular*** Weight |
|---|---|---|
| Sandoz 32337-15-4A | 0.55–0.56 | 19,400 |
| Dynatech 15191-2 | 1.04 | 34,255 |
| Dynatech 19665-1 | — | 117,000 |
| Southern Research | — | 220,000 |
| Armour #25450 | — | 419,000 |

**Determined in benzene at 30° C.
***Number average molecular weight determined by end group analysis.

The internal phase or drugs employed were micronized gelatin (Armour), 10% salmon calcitonin in gelatin (Armour) and Hydergine (Sandoz). The amount employed was 28 to 500 mg./0.5 or 1.0 g dl-PLA.

Once the polymer solution was prepared, it was adjusted to a specified temperature at which point the drug was added. After the drug was dispersed, a low molecular weight polybutadiene polymer (marketed under the trade designation "Lithene PH") was added as a 60 vol. % solution in toluene as the phase separation agent. Ten ml. of this solution were added. This caused phase separation of the dl-PLA from the solution and the system was allowed to equilibrate 5 to 10 min. before n-heptane was added as the nonsolvent to isolate the microcapsules as described in the earlier examples.

The results are set forth in Tables XII through XVII. In these tables, the following terms are used. Coacervation temperature (coac. temp., °C.) means the temperature at which the phase inducer or phase separation agent was added to the dl-PLA solution. The drug was added at the same temperature but before the phase inducer addition. Isolation temperature (°C.) is the temperature at which n-heptane as the nonsolvent was added to the encapsulation system. Theoretical payload (theo. payload, wt. %) is 100 times the weight of drug added to the encapsulation reactor divided by the total weight of dl-PLA and drug. The Sieve Analysis gives the weight of each capsule fraction (gm.) isolated after the contents of an encapsulation reactor were sieved through 300µ, 180µ, 106µ and 63µ screens. The screens used had square openings with these dimensions and the results are reported as weight of capsules retained by the screens but passed by the next higher size opening screen. The term NM means not measurable referring to the cases where the weight of capsules in a number of capsule fractions was too small to measure (or zero). The total weight of capsules isolated (total wt. isolated, gm.) is the sum of all fractions. The theoretical total weight (theo. total wt. gm.) is the total weight of dl-PLA and drug added to the encapsulation reactor. The yield (% theory) is 100 times the total weight of capsules isolated divided by the total weight of dl-PLA and drug originally placed in the encapsulation reactor.

TABLE XII
Tabulation of Capsule Runs Make with Sandoz 32337-15-4A dl-PLA*

Part A

| Capsule sample | 1 | 2 | 3 | 4 | 5 |
|---|---|---|---|---|---|
| Coac. temp., °C. | −51 | −50 | −40 | −10 | +25 |
| Isolation temp., °C. | −70 | −50 | −36 to −41 | −20 | +25 |
| Theo. payload, wt. %** | 33+ | 5.7 | 5.9 | 5.5 | 9.0 |
| Sieve analysis: | | | | | |
| >300μ, gm | 0.013 | 0.045 | 1.166 | 1.197 | 1.279*** |
| 180–300μ, gm | 0.043 | 0.002 | 0.025 | 0.010 | 0.033 |
| 106–180μ, gm | 0.855 | 0.222 | 0.017 | 0.004 | NM |
| 63–106μ, gm | 0.060 | 0.700 | 0.004 | NM | NM |
| <63μ, gm | 0.012 | 0.189 | NM | NM | NM |
| Total wt. isolated, gm | 0.983 | 1.158 | 1.212 | 1.201 | 1.312 |
| Wt. of drug, mg | 500.00 | 60.00 | 63.00 | 58.00 | 99.00 |
| Theo. total wt., gm | 1.50 g | 1.060 | 1.063 | 1.058 | 1.099 |
| Yield, % theo. | 65.5 | 109.2 | 114.0 | 113.5 | 119.4 |

*All capsules prepared by standard encapsulation procedure with 1.0 g dl-PLA/40 ml toluene and Lot 151 Lithene PH
**Armour micronized gelatin K-735074-1
***1.260 g of this fraction was in a single blob
+Hydergine is the drug encapsulated in this run

Part B

| Capsule sample | 6 | 7 | 8 | 9 |
|---|---|---|---|---|
| Coac. temp., °C. | −50 | −50 | −50 | −40 |
| Isolation temp., °C. | −71 | −60 | −50 | −40 |
| Theo. payload, wt. %** | 6.4 | 6.1 | 6.3 | 5.4 |
| Sieve analysis: | | | | |
| >300μ, gm | 0.022 | 1.141 | 1.273*** | 1.340**** |
| 180–300μ, gm | 0.010 | 0.054 | 0.007 | 0.016 |
| 106–180μ, gm | 0.233 | 0.058 | NM | NM |
| 63–106μ, gm | 0.477 | 0.030 | NM | NM |
| <63μ, gm | 0.239 | NM | NM | NM |
| Total wt. isolated, gm | 0.981 | 1.283 | 1.280 | 1.356 |
| Wt. of drug, mg | 68.00 | 65.00 | 67.00 | 57.00 |
| Theo. total wt., gm | 1.068 | 1.065 | 1.067 | 1.057 |
| Yield, % theo. | 91.9 | 120.5 | 120.0 | 128.0 |

*All capsules prepared by standard encapsulation procedure with 1.0 g dl-PLA/40 ml toluene and Lot 292-B Lithene PH
**Armour micronized gelatin K-735074-1
***1.162 g of this fraction was in a single blob
****1.034 g of this fraction was in a single blob

Part C

| Capsule sample | 10 | 11 |
|---|---|---|
| Coac. temp., °C. | −50 | −50 |
| Isolation temp., °C. | −70 | −50 |
| Theo. payload, wt. %** | 5.7 | 6.5 |
| Sieve analysis: | | |
| >300μ, gm | 0.025 | 0.570 |
| 180–300μ, gm | 0.006 | 0.012 |
| 106–180μ, gm | 0.096 | 0.012 |
| 63–106μ, gm | 0.315 | NM |
| <63μ, gm | 0.177 | NM |
| Total wt. isolated, gm | 0.619 | 0.594 |
| Wt. of drug, mg | 30.00 | 35.00 |
| Theo. total wt., gm | 0.530 | 0.535 |
| Yield, % theo. | 116.8 | 111.0 |

*All capsules prepared by standard encapsulation procedure with 0.5 g dl-PLA/40 ml toluene and Lot 292-B Lithene PH
**Armour micronized gelatin K-735074-1

TABLE XIII
Tabulation of Capsule Runs Make with Dynatech 15191-2 dl-PLA*

| Capsule sample | 1 | 2 | 3 | 4 | 5 |
|---|---|---|---|---|---|
| Coac. temp., °C. | −50 | −40 | −20 to −28 | −5 ± 2 | +25 |
| Isolation temp., °C. | −70 | −40 ± 3 | −23 to −30 | −5 ± 2 | +25 |
| Theo. payload, wt. %** | 7.4 | 5.4 | 5.4 | 5.5 | 5.6 |
| Sieve analysis: | | | | | |
| >300μ, gm | 0.010 | 0.086 | 1.161 | 1.045 | 0.591 |
| 180–300μ, gm | 0.007 | 0.066 | 0.185 | 0.058 | 0.057 |
| 106–180μ, gm | 0.012 | 0.287 | 0.261 | 0.384 | 0.006 |
| 63–106μ, gm | 0.056 | 0.205 | 0.052 | 0.078 | NM |
| <63μ, gm | 0.390 | 0.044 | 0.077 | 0.003 | NM |
| Total wt. isolated, gm | 0.475 | 0.688 | 0.666 | 0.568 | 0.654 |
| Wt. of drug, mg | 40.00 | 34.00 | 35.00 | 29.00 | 34.00 |
| Theo. total wt., gm | 0.540 | 0.534 | 0.535 | 0.529 | 0.534 |
| Yield, % theo. | 88.0 | 128.8 | 124.5 | 107.4 | 122.5 |

*All capsules prepared by standard encapsulation procedure with 0.5 g dl-PLA/40 ml toluene
**Armour micronized gelatin K-735074-1

TABLE XIV
Tabulation of Capsule Runs Make with Dynatech 19665-1 dl-PLA

| Capsule sample | 1 | 2 | 3 |
|---|---|---|---|
| Coac. temp., °C. | −50 to −55 | −52 | −30 |
| Isolation temp., °C. | −70 | −50 to −52 | −30 |
| Theo. payload, wt. %** | 5.8 | 5.9 | 5.8 |
| Sieve analysis: | | | |
| >300μ, gm | 0.035 | 0.561 | 0.686 |
| 180–300μ, gm | 0.066 | 0.069 | 0.038 |
| 106–180μ, gm | 0.317 | 0.021 | 0.008 |
| 63–106μ, gm | 0.180 | 0.004 | 0.001 |
| <63μ, gm | 0.023 | NM | NM |
| Total wt. isolated, gm | 0.621 | 0.655 | 0.733 |
| Wt. of drug, mg | 34.00 | 28.00 | 31.00 |
| Theo. total wt., gm | 0.534 | 0.528 | 0.531 |
| Yield, % theo. | 116.3 | 124.1 | 138.0 |

*All capsules prepared by standard encapsulation procedure with 0.5 g dl-PLA/40 ml toluene and Lot 292-B Lithene PH
**Armour micronized gelatin K-735074-1

TABLE XV
Tabulation of Capsule Runs Make with Dynatech 19665-1 dl-PLA

| Capsule sample | 1 | 2 | 3 |
|---|---|---|---|
| Coac. temp., °C. | −50 | −50 | −25 |
| Isolation temp., °C. | −70 | −50 | −25 |
| Theo. payload, wt. %** | 5.7*** | 5.5 | 5.8 |
| Sieve analysis: | | | |
| >300μ, gm | 0.048 | 0.499 | 0.721**** |
| 180–300μ, gm | 0.195 | 0.042 | NM |
| 106–180μ, gm | 0.273 | 0.012 | NM |
| 63–106μ, gm | 0.063 | 0.001 | NM |
| <63μ, gm | 0.004 | — | NM |
| Total wt. isolated, gm | 0.583 | 0.554 | 0.721 |
| Wt. of drug, mg | 30.00 | 29.00 | 33.00 |
| Theo. total wt., gm | 0.530 | 0.529 | 0.533 |
| Yield, % theo. | 110 | 104.7 | 135.3 |

*All capsules prepared by standard encapsulation procedure with 0.5 g dl-PLA/40 ml toluene and Lot 292-B Lithene PH
**Armour micronized gelatin K-735074-1
***Armour micronized 10% salmon calcitonin in gelatin, Lot K-735074-2.
****All in one big blob (i.e., no particles formed)

TABLE XVI
Tabulation of Capsule Run Made With Armour #25450 dl-PLA*

| | |
|---|---|
| Coac. temp., °C. | −50 |
| Isolation temp., °C. | −70 |

TABLE XVI-continued

Tabulation of Capsule Run Made With
Armour #25450 dl-PLA*

| | |
|---|---|
| Theo. payload, wt. %** | 7.4 |
| Sieve analysis: | |
| >300μ, gm | 0.622*** |
| 180-300μ, gm | 0.006 |
| 106-180μ, gm | 0.003 |
| 63-106μ, gm | NM |
| <63μ, gm | NM |
| Total wt. isolated, gm | 0.631 |
| Wt. of drug, mg. | 46.00 |
| Theo. total wt., gm | 0.546 |
| Yield, % theory | 115.5 |

*All capsules prepared by standard encapsulation procedure with 0.5 g dl-PLG/40 ml. toluene
**Armour micronized gelatin K-735074-1
***0.420 g was in a single glob.

TABLE XVII

Comparison of Encapsulation Runs Made In Toluene and Trichloroethylene with Sandoz 32337-15-4A dl-PLA*

| Capsule sample | 1 | 2 |
|---|---|---|
| Solvent | Toluene | Trichloroethylene |
| Coac. temp., °C. | -50 | -50 |
| Isolation temp., °C. | -70 | -70 |
| Theo. payload, wt. %** | 5.7 | 5.7 |
| Sieve analysis: | | |
| >300μ, gm | 0.025 | 0.141 |
| 180-300μ, gm | 0.006 | 0.139 |
| 106-180μ, gm | 0.096 | 0.122 |
| 63-106μ, gm | 0.315 | 0.099 |
| <63μ, gm | 0.177 | 0.064 |
| Total wt. isolated, gm | 0.619 | 0.565 |
| Wt. of drug, mg | 30.00 | 35.00 |
| Theo. total wt., gm | 0.530 | 0.530 |
| Yield, % theo. | 116.8 | 106.6 |

*All capsules prepared by standard encapsulation procedure with 0.5 g dl-PLA/40 ml toluene and Lot 292-B Lithene PH
**Armour micronized gelatin K-735074-1

EXAMPLE 22 dl-Poly(lactic acid) polymer (1.000 g.) was dissolved in toluene (40 ml.) and filtered to remove fibrous particles by means of a plug of glass wool. The solution was cooled to -64° F. and 0.300 g. Hydergine GA-54 (Sandoz) was added with stirring. Six ml. of liquid polybutadiene ("Lithene PH") was brought to a volume of 10 ml. total solution by the addition of 4 ml. toluene. This solution was placed in a separatory funnel and added dropwise to the polymer-drug mixture.

| Addition | No. Drops | Temperature | Stirring Speed |
|---|---|---|---|
| 1 | 100 | -60° F. | 20 rev./9 sec. |
| 2 | 51 | -62° F. | 20 rev./9 sec. |
| 3 | 57 | -60° F. | 20 rev./9 sec. |
| 4 | 49 | -60° F. | 20 rev./9 sec. |
| 5 | 47 | -60° F. | 20 rev./9 sec. |
| | 304 | | |

The temperature was then reduced to -90° F. and the dropwise addition of n-heptane was begun very slowly at first, and then adjusted to 8-10 drops per sec. After completion of the heptane addition, the microcapsules which had formed were washed four times with heptane by decantation and filtered. The microcapsules were then put in the vacuum oven for drying at room temperature.

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. In a process for the preparation of microcapsules having a particulate core material encapsulated by a polymeric coating wherein the polymer is first dissolved in a solvent in which the core material is not soluble, the polymer is precipitated by phase separation to encapsulate the core material by the addition of a phase separation agent to the polymer-core material-solvent system to form microcapsules of the core material having walls constituted by the polymer, and the microcapsules are thereafter isolated, the improvement which comprises isolating said microcapsules at a temperature at least as low as -30° C.

2. The process according to claim 1 wherein the temperature is from about -30° C. to about -70° C.

3. The process according to claim 1 wherein the temperature is about -70° C.

4. The process according to claim 1 wherein the core material is a solid, injectable drug.

5. The process according to claim 4 wherein the drug is equilibrated in a humid environment before being encapsulated.

6. The process according to claim 4 wherein the drug is hygroscopic and access of moisture to the drug is restricted before and during encapsulation of the drug.

7. The process according to claim 4 wherein the polymer is a bioabsorbable polymer selected from the group consisting of poly (lactic acid) polymers, poly (glycolic acid) polymers, poly (hydroxybutyric acid) polymers and lactide/glycolide copolymers.

8. The process according to claim 7 wherein the polymer is a poly (lactic acid) polymer.

9. The process according to claim 8 wherein the core material is selected from the group consisting of cyclazocine, tetracycline, ethisterone, digitoxin, antimony potassium tartrate, salmon calcitonin, ACTH, lypressin, sommatostatin, and insulin.

10. The process according to claim 8 wherein the solvent is selected from the group consisting of toluene, xylene, benzene, chloroform, cyclohexane, methyl ethyl ketone, ethyl acetate, n-butanol, isopropanol, methanol, acetone, ethanol, tetrachloroethylene and mixtures thereof.

11. The process according to claim 1 wherein the phase separation agent is selected from the group consisting of polybutadiene, polybutadiene-methylstyrene copolymers, polyisobutylene, polystyrene, poly (vinyl pyrrolidone), silicone fluids, and poly (methyl vinyl ether and comaleic anhydride half ester) and blends thereof with natural oils.

12. The process according to claim 1 wherein said microcapsules are isolated by addition to said system of a nonsolvent for said polymer.

13. The process according to claim 12 wherein said nonsolvent for said polymer is relatively volatile and the microcapsules are separated therefrom by volatilization of the nonsolvent.

14. The process according to claim 12 wherein said nonsolvent for said polymer is added to said system at a relatively slow rate.

15. The process according to claim 12 wherein said nonsolvent for said polymer is selected from the group consisting of alkanes, fluorinated hydrocarbons, hydrogenated naphthalenes and mineral spirits.

16. The process according to claim 15 wherein said nonsolvent for said polymer is n-heptane.

* * * * *